US008551400B2

(12) United States Patent
Fei et al.

(10) Patent No.: US 8,551,400 B2
(45) Date of Patent: Oct. 8, 2013

(54) ANALYTE SENSORS, TESTING APPARATUS AND MANUFACTURING METHODS

(75) Inventors: Jiangfeng Fei, Sleepy Hollow, NY (US); Raeann Gifford, Cortlandt Manor, NY (US); Narasinha Parasnis, Nanuet, NY (US); Serban Peteu, East Lansing, MI (US); Hoi-Cheong Steve Sun, Mount Kisco, NY (US); Yuan Wang, Mountain Lakes, NJ (US); Mu Wu, Hopewell Junction, NY (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 13/119,209

(22) PCT Filed: Sep. 17, 2009

(86) PCT No.: PCT/US2009/057264
§ 371 (c)(1),
(2), (4) Date: Mar. 16, 2011

(87) PCT Pub. No.: WO2010/033668
PCT Pub. Date: Mar. 25, 2010

(65) Prior Publication Data
US 2011/0171071 A1 Jul. 14, 2011

Related U.S. Application Data

(60) Provisional application No. 61/098,720, filed on Sep. 19, 2008.

(51) Int. Cl.
*G01N 15/06* (2006.01)
*G01N 33/00* (2006.01)
*G01N 33/48* (2006.01)

(52) U.S. Cl.
USPC ............ 422/50; 422/52; 422/400; 422/402; 422/68.1; 422/82.05; 422/82.06; 422/83

(58) Field of Classification Search
USPC ............... 422/50, 52, 400, 402, 68.1, 82.05, 422/82.06, 83
See application file for complete search history.

(56) References Cited

U.S. PATENT DOCUMENTS 4,326,927 A 4/1982 Stetter et al.
4,596,741 A * 6/1986 Endou et al. .................. 428/368

(Continued)

FOREIGN PATENT DOCUMENTS

WO WO 2006/057722 6/2006
WO WO 2009/100082 8/2009

(Continued)

OTHER PUBLICATIONS

Singh et al., "SiC-C Fiber Electrode for Biological Sensing", Feb. 22, 2007, Materials Science and Engineering C, Elsevier Science S.A., vol. 27, No. 3, pp. 551-557.

(Continued)

*Primary Examiner* — Brian J Sines
(74) *Attorney, Agent, or Firm* — Dugan & Dugan, PC

(57) ABSTRACT

In some aspects, an analyte sensor is provided for detecting an analyte concentration level in a bio-fluid sample. The analyte sensor may include a first sensor member coupled to a base, wherein the first sensor member includes a semiconductor material, a second sensor member coupled to the base; and an active region in contact with at least the first sensor member. In some aspects, the first sensor member may be a fiber, and may have a conductive core and a semiconducting cladding surrounding the core. Manufacturing methods and apparatus utilizing the sensors are provided, as are numerous other aspects.

18 Claims, 9 Drawing Sheets

(56) References Cited

U.S. PATENT DOCUMENTS

| | | | |
|---|---|---|---|
| 5,431,800 | A | 7/1995 | Kirchhoff et al. |
| 5,476,776 | A | 12/1995 | Wilkins |
| 5,611,900 | A | 3/1997 | Worden et al. |
| 5,627,922 | A | 5/1997 | Kopelman et al. |
| 5,666,353 | A | 9/1997 | Klausmeier et al. |
| 5,777,372 | A | 7/1998 | Kobashi |
| 5,866,353 | A | 2/1999 | Berneth et al. |
| 6,218,661 | B1 * | 4/2001 | Schroeder et al. ....... 250/227.14 |
| 6,521,109 | B1 | 2/2003 | Bartic et al. |
| 6,743,635 | B2 | 6/2004 | Neel et al. |
| 7,074,519 | B2 | 7/2006 | Kuhr et al. |
| 7,951,632 | B1 | 5/2011 | Quick et al. |
| 2002/0137998 | A1 | 9/2002 | Smart et al. |
| 2002/0168290 | A1 | 11/2002 | Yuzhakov et al. |
| 2002/0177763 | A1 | 11/2002 | Burns et al. |
| 2003/0217918 | A1 | 11/2003 | Davies et al. |
| 2004/0002682 | A1 | 1/2004 | Kovelman et al. |
| 2004/0039303 | A1 | 2/2004 | Wurster et al. |
| 2004/0094432 | A1 | 5/2004 | Neel et al. |
| 2004/0136866 | A1 | 7/2004 | Pontis et al. |
| 2004/0146863 | A1 | 7/2004 | Pisharody et al. |
| 2004/0200721 | A1 | 10/2004 | Bhullar et al. |
| 2004/0254546 | A1 | 12/2004 | Lefebvre |
| 2005/0183953 | A1 | 8/2005 | Su et al. |
| 2005/0238537 | A1 | 10/2005 | Say et al. |
| 2005/0261606 | A1 | 11/2005 | Sohrab |
| 2005/0279647 | A1 | 12/2005 | Beaty |
| 2005/0287065 | A1 | 12/2005 | Suddarth et al. |
| 2006/0113187 | A1 | 6/2006 | Deng et al. |
| 2006/0211933 | A1 | 9/2006 | Zimmermann et al. |
| 2007/0087492 | A1 | 4/2007 | Yamanaka |
| 2007/0096164 | A1 | 5/2007 | Peters et al. |
| 2008/0027302 | A1 | 1/2008 | Buse et al. |
| 2008/0197024 | A1 | 8/2008 | Simpson et al. |
| 2010/0298679 | A1 | 11/2010 | Wu et al. |
| 2011/0180405 | A1 | 7/2011 | Chinnayelka |

FOREIGN PATENT DOCUMENTS

| | | |
|---|---|---|
| WO | WO 2010/033660 | 3/2010 |
| WO | WO 2010/033668 | 3/2010 |
| WO | WO 2010/033741 | 3/2010 |
| WO | WO 2010/033748 | 3/2010 |

OTHER PUBLICATIONS

International Search Report and Written Opinion of related International Application No. PCT/US2009/057264 mailed Nov. 10, 2009.

International Preliminary Report on Patentability of related International Application No. PCT/US2009/057264 mailed Mar. 31, 2011.

Isao Karube et al., "Integrated Microbiosensors for Medical Use", Dec. 1, 1989, Annals of New York Academy of Sciences, vol. 542, No. 9, pp. 470-479.

International Preliminary Report on Patentability and Written Opinion of International Application No. PCT/US2009/032991 mailed Aug. 19, 2010.

International Search Report and Written Opinion of related International Application No. PCT/US2009/057253 mailed Nov. 2, 2009.

International Search Report and Written Opinion of International Application No. PCT/US2009/057372 mailed Nov. 13, 2009.

International Preliminary Report on Patentability of related International Application No. PCT/US09/057382 mailed Mar. 31, 2011.

International Search Report and Written Opinion of International Application No. PCT/US09/057382 mailed Feb. 1, 2010.

International Preliminary Report on Patentability and Written Opinion of related International Application No. PCT/US2009/057372 mailed Mar. 31, 2011.

International Preliminary Report on Patentability Search Report and Written Opinion of related International Application No. PCT/US2009/057253 mailed Mar. 31, 2011.

International Search Report and Written Opinion of International Application No. PCT/US2009/032991 mailed Aug. 6, 2009.

Communication pursuant to Rules 161(2) and 162 EPC of related European Application No. 09815226.7 May 12, 2011.

Communication pursuant to Rules 161(2) and 162 EPC of related European Application No. 09815166.5 May 13, 2011.

Communication pursuant to Rules 161(2) and 162 EPC of related European Application No. 09815223.4 May 12, 2011.

Communication pursuant to Rules 161(2) and 162 EPC of related European Application No. 09815172.3 May 25, 2011.

Extended Search Report of related European Application No. 09815223.4 dated Oct. 2, 2012.

Communication pursuant to Rules 70(2) and 70a(2) EPC of related European Application No. 09815223.4 dated Oct. 19, 2012.

Schackleford et al., CRC Materials Science and Engineering Handbook, 3rd ed., 2000, Table 154.

Extended Search Report of related European Application No. 09815166.5 dated Oct. 22, 2012.

* cited by examiner

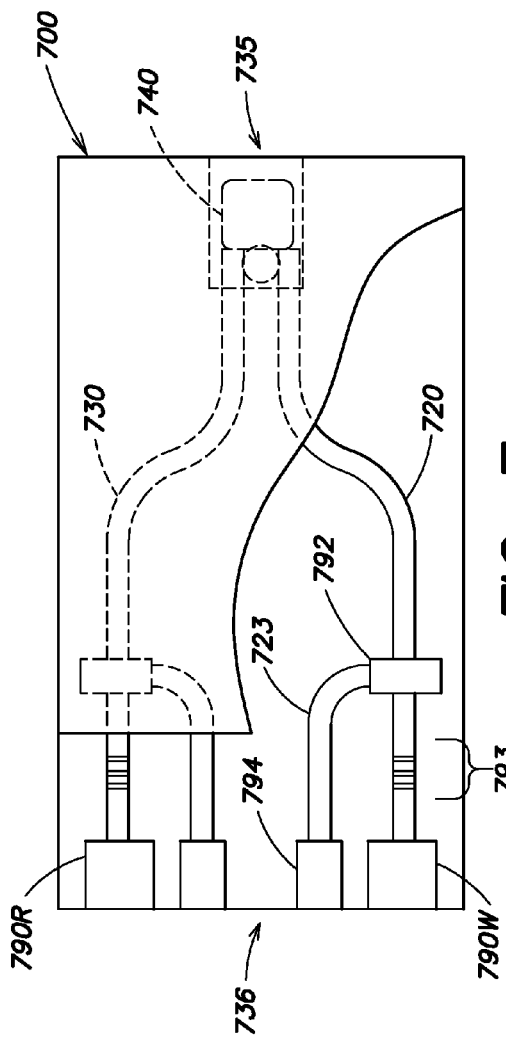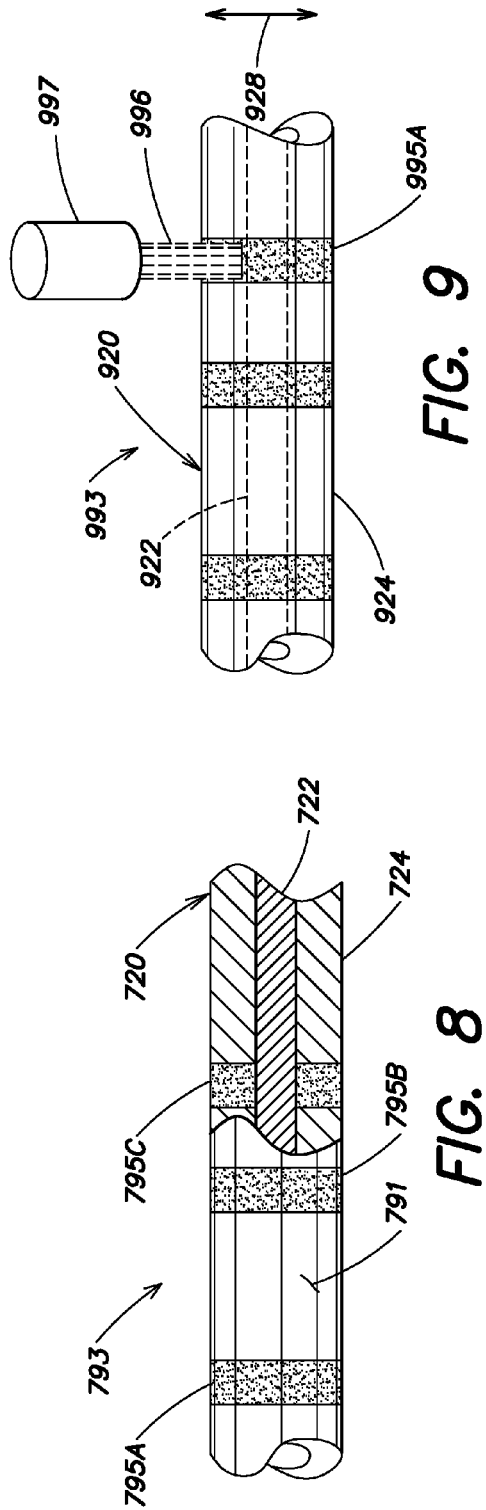

ANALYTE SENSORS, TESTING APPARATUS AND MANUFACTURING METHODS

RELATED APPLICATIONS

The present application claims priority to U.S. Provisional Patent Application No. 61/098,720 filed Sep. 19, 2008, and entitled "ANALYTE SENSORS AND MANUFACTURING METHODS" which is hereby incorporated herein by reference in its entirety for all purposes.

FIELD OF THE INVENTION

The present invention relates to electrochemical analyte sensors that may be used to detect an analyte concentration level in a bio-fluid sample, apparatus including the analyte sensors, and methods of manufacturing thereof.

BACKGROUND OF THE INVENTION

The monitoring of analyte concentration levels in a bio-fluid may be an important part of health diagnostics. For example, an electrochemical analyte sensor may be employed for the monitoring of a patient's blood glucose level as part of diabetes treatment and care.

An electrochemical analyte sensor may be employed discretely ('discrete monitoring'), for instance, by detecting an analyte concentration level in bio-fluid sample such as from a single sample of blood or other interstitial fluid obtained from the patient via a lancet (e.g., by a pin-prick or needle). Optionally, the analyte sensor may be employed continuously ('continuous monitoring'), by implanting the sensor in the patient for a duration of time. In discrete monitoring, there may be a separation between the bio-fluid sample collection process and the measurement of the analyte concentration level. Typically, after a bio-fluid sample has been obtained from the patient, such as by the use of a lancet, the sample may then be transferred to a medium (e.g., a test strip sensor or a detector) for measurement of the bio-fluid sample's analyte concentration level.

Because conventional electrochemical analyte sensors may have relatively low sensitivity and because transfer of the bio-fluid sample to the sensor may be relatively inefficient, a relatively large sample volume may be required in order to yield an accurate measurement of the analyte concentration level. In such instances, if the provided sample has an insufficient sample volume, then either no reading or an inaccurate reading may result. Accordingly, an additional bio-fluid sample may need to be drawn and, consequently, lancet insertion may need to be repeated which may cause further pain and discomfort to the patient.

Additionally, conventional sensors may require the use of precious metals for the working and/or reference/counter electrodes which may add significantly to the cost of the analyte sensors.

It may, therefore, be beneficial to provide an analyte sensor adapted for bio-fluid analyte sampling that may consistently provide for analyte concentration level measurements from an obtained bio-fluid sample, which may require a lessened sample volume, and/or which may also provide for lower cost manufacture.

SUMMARY OF THE INVENTION

In a first aspect, the present invention provides an analyte sensor including a base; a first sensor member coupled to the base, the first sensor member comprising a semiconductor material; a second sensor member coupled to the base and spaced from the first sensor member; and an active region in contact with at least the first sensor member.

In another aspect, the present invention provides an analyte sensor for detecting an analyte concentration level in a bio-fluid sample, including a base; a first sensor member coupled to the base and comprised of a semiconductor material; a cavity formed proximate to an end of the first sensor member; and an active region positioned within the cavity, the active region being coupled to an end of the first sensor member.

In another aspect, the present invention provides an analyte sensor for detecting an analyte concentration level in a bio-fluid sample, including a base; a fiber sensor member coupled to the base, the fiber sensor member including at least a portion which is made of a semiconductor material; a cavity formed proximate to an end of the fiber sensor member; and an active region positioned within the cavity, the active region being coupled to an end of the fiber sensor member.

In yet another aspect, the present invention provides an analyte sensor for detecting an analyte concentration level in a bio-fluid sample, including an insulating base, a first sensor member coupled to the base and comprised of a core of conductive material and a cladding of a semiconductor material surrounding the core, a second sensor member coupled to the base and comprised of a core of conductive material and a cladding of a semiconductor material surrounding the core, a cavity formed proximate to ends of the first and second sensor members, an active region positioned within the cavity, the active region being coupled to both the first and second sensor members, and a lid attached to the insulating base wherein the base and lid at least partially defining the cavity.

In another aspect, the present invention provides a testing apparatus, including a port receiving an analyte sensor, wherein the analyte sensor further comprises a base; a first sensor member coupled to the base, the first sensor member comprising a semiconductor material; a second sensor member coupled to the base and spaced from the first sensor member; and an active region in contact with at least the first sensor member.

In a method aspect, the present invention provides a method of manufacturing an analyte sensor including the steps of providing a base; mounting a first sensor member on the base wherein the first sensor member is comprised of a semiconductor material; applying an active region on a portion of the first sensor member; and providing a lid coupled to the base.

In another method aspect, the present invention provides a method of manufacturing analyte sensors, including the steps of providing a sheet of base material; mounting a plurality of fibers on the sheet of base material wherein the fibers are comprised of a semiconductor material; applying an active region on at least some of the fibers; attaching lidstock to form a unitary body; and cutting the unitary body to provide a plurality of analyte sensors.

Other features and aspects of the present invention will become more fully apparent from the following detailed description, the appended claims and the accompanying drawings.

BRIEF DESCRIPTION OF THE DRAWINGS

FIG. 7 is a top view of another exemplary embodiment of an analyte sensor according to the present invention.

FIG. 8 is a enlarged partially cross-sectioned view of a coded region of the analyte sensor embodiment of FIG. 7 according to the present invention.

FIG. 9 is a diagram illustrating a formation of conductive tracks on a sensor member included within an exemplary embodiment of an analyte sensor according to the present invention.

DETAILED DESCRIPTION

According to an aspect of the present invention, an analyte sensor is provided that includes a first sensor member, such as a fiber comprised of a semiconductor material (e.g., silicon carbide (SiC)). The first sensor member may be mounted on a base (e.g., of an insulating material). In some embodiments, the first sensor member may include a conductive core which may comprise a part of a working electrode of the analyte sensor and a cladding comprised of the semiconductor material. An active region may be provided in contact with at least the first sensor member. For example, the active region may be in contact with, and electrically coupled to, the first sensor member such that analyte detection may be accomplished by connection to a testing apparatus. A second sensor member may also be mounted on the base, wherein the second sensor may operate as a reference or counter electrode. The second sensor member may also include a semiconductor material, and in some embodiments, may be comprised of a conductive core and a cladding comprised of a semiconductor material. Similarly, the second sensor member may be in contact with, and electrically coupled to, the active region. In some embodiments, the conductive core of the first sensor member and even the second sensor member may comprise carbon (e.g., graphite) and the cladding may comprise silicon carbide.

Additionally, the analyte sensor may include a cavity, which may be located proximate to an end of the first sensor member and the active region. The cavity may be adapted for accepting a bio-fluid sample. The term "cavity" as defined herein is a hollow, indented, or concave area having walls adapted to contain and confine the bio-fluid sample. In some embodiments, the cavity may be at least partially formed and defined by the base and a lid, which is coupled to the base.

The active region of the analyte sensor may include one or more catalytic agents and/or reagents adapted to react and convert an analyte in the bio-fluid sample received in the cavity into reaction products from which an electrical current may be generated. The resulting electrical current may flow in the first sensor member (e.g., in the core and/or cladding). The first sensor member, in some embodiments, forms at least a portion of a working electrode. The generated electrical current may then be detected, such as by testing apparatus (e.g., an ammeter) connected to the working electrode, thereby enabling a determination and readout of an analyte concentration level contained in the bio-fluid sample. The electrical current provided may have a magnitude correlated with the concentration of the analyte in the sample, for example.

These and other embodiments of analyte sensors, apparatus including the analyte sensors and methods for manufacturing the analyte sensors are described below with reference to FIGS. 1-13.

Figure 1:
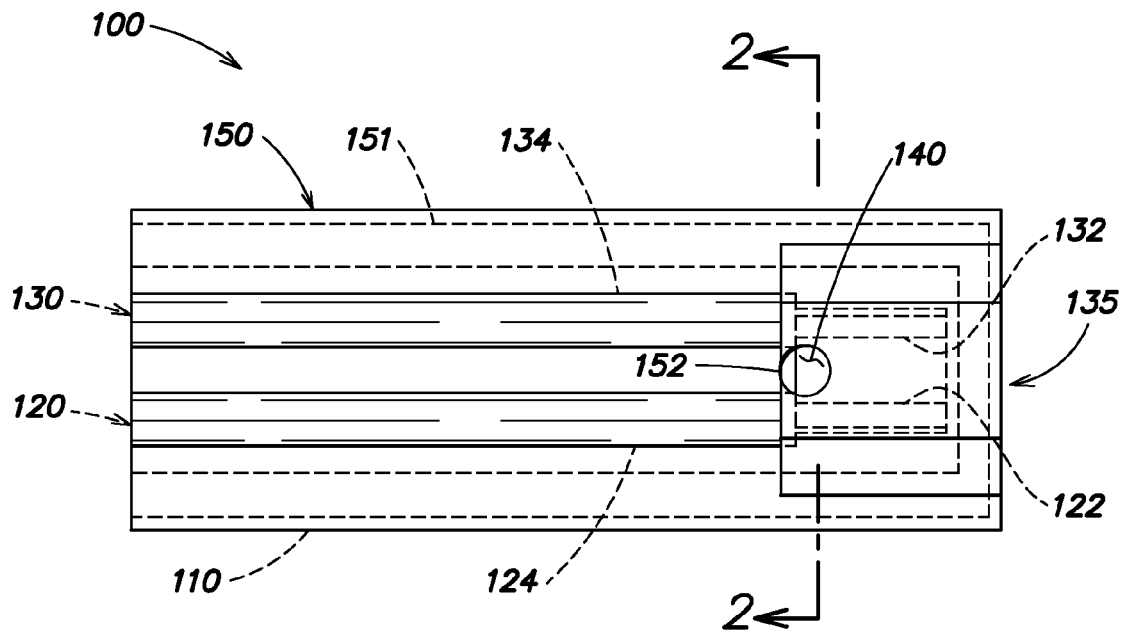
FIG. 1 is a top view of an exemplary embodiment of an analyte sensor provided according to the present invention.
Figure 2:
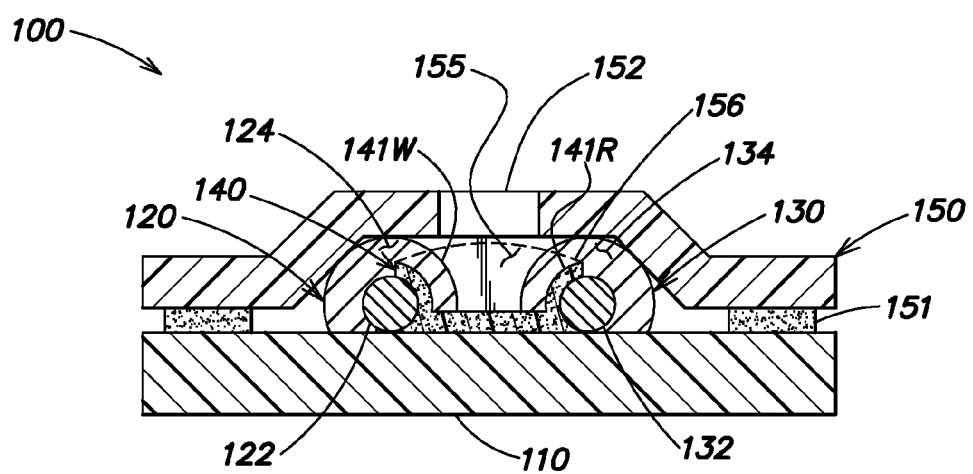
FIG. 2 is an enlarged cross-sectional view of the analyte sensor of FIG. 1 taken along section line 2-2.
Figure 3:
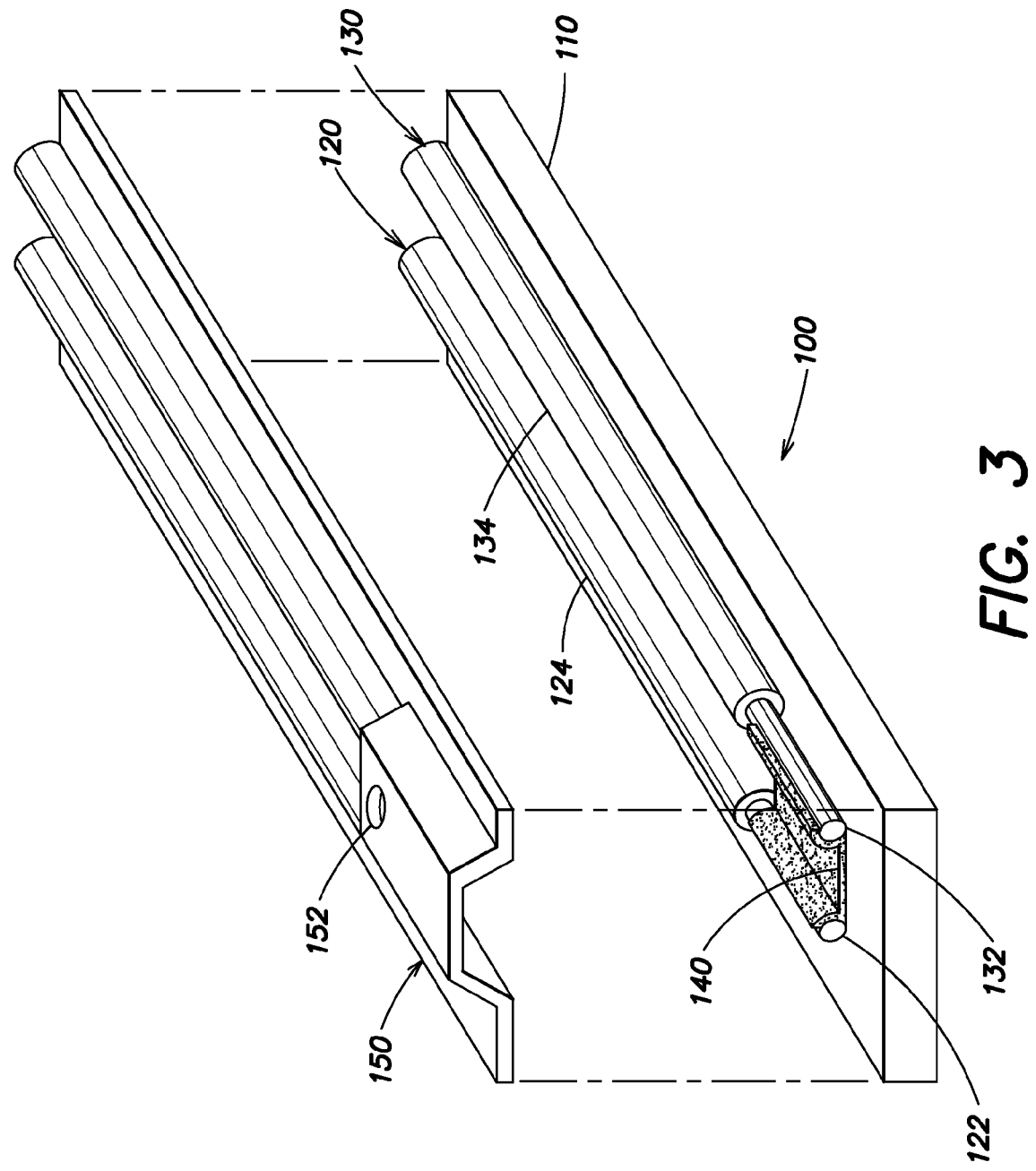
FIG. 3 is an exploded isometric view of the exemplary embodiment of the analyte sensor of FIG. 1 according to the present invention showing a lid being separated for clarity.

FIGS. 1-3 show various views of a first exemplary embodiment of an analyte sensor 100 provided according to the present invention. The analyte sensor 100 may include a base 110 preferably formed of an insulating material. The base 110 may have a first sensor member 120 mounted thereon. The base 110 may be manufactured from of a polymer material, such as a polycarbonate, polyethylene terephthalate, polyimide, high-density polyethylene, or polystyrene material, for example. Further, the first sensor member 120 may be mounted on the base 110 by including some level of physical impression into the base 110. For example, when the base 110 is a deformable polymer, sufficient pressure and/or heat may be applied thereby causing the first sensor member 120 to form an impression in the base 110. Optionally, the impression may be molded into the base 110. Optionally, the first sensor member 120 may be adhered, glued, heat fused, ultrasonically fused, or otherwise mounted to the base 110. In some embodiments, the first sensor member 120 may be mounted to the base 110 simply by sandwiching between the base 110 and a lid 150. The size and shape of the base 110 is not of consequence and any suitable size and shape may be used. The base 110 simply functions as a way of mounting the sensor member 120 and to allow ease of handling by the user.

The first sensor member 120 may include a semiconductor material. For example, the sensor member 120 may include a core 122 comprised of a conductive material and the cladding 124 which is comprised of a semiconductor material. Preferably, the first member 120 is a fiber or filament with a length much greater than its width. In some embodiments, the fiber may include the conducting core 122, which may be at least partially surrounded by the cladding 124. In the exemplary embodiment shown, the cladding 124 may include an annular shape, which may fully surround the core 122 along at least a portion of the length of the core 122. The core 122 may comprise the shape of a cylindrical rod, for example. Both the core 122, which may include the conductive material, and the cladding 124, which may include the semiconductor material, in operation may convey electrical current, albeit the semiconductor material may include a much higher resistivity as compared to the core 122 and, therefore, may carry less current than the core 122. In some embodiments, the core 122 may comprise carbon (e.g. graphite) and the cladding 124 may comprise silicon carbide (SiC). SiC/C fibers having a suitable SiC cladding and carbon core are manufactured by Specialty Materials Inc. of Lowell, Mass., for example. However, the conductive material of the core 122 may also comprise other electrically conductive metal materials including the noble metals (e.g., gold, silver, platinum, etc.), copper and aluminum. The cladding 124 may comprise other semiconductor materials including Group IV elements such as silicon and germanium, Group IV compounds such as silicon germanide (SiGe), and Group III-V compounds such as gallium arsenide (GaAs) and indium phosphide (InP), among others. In some embodiments, a semiconducting fiber with no conductive core may be used.

In some embodiments, the first sensor member 120 may have a total diameter (including the core 122 and cladding 124) of about 150 microns more less, about 100 microns or less, about 75 microns or less, or even about 50 microns or less, and between about 50 microns and about 150 microns in some embodiments (although larger or smaller sizes also may be used). The core 122 may have a diameter between about 10 to about 100 microns, or even between about 20 microns to about 40 microns, and preferably about 30 microns, although other dimensions may also be used. In the depicted embodiment, the first sensor member 120 may include an end portion where the core 122 is exposed (the 'stripped end'). This may enlarge and enhance the effective contact area, and thus the conducting area, of the conductive core 122 such as when the core 122 functions as an electrode. Any suitable technique may be used to remove the cladding material thereby forming the stripped end, such as machining, etching, or the like. Electrochemical wet etching with an acid (e.g., HN, HCF or combinations) may be used. Other mechanisms for enhancing the effective contact area of the core are described below.

Figure 5:
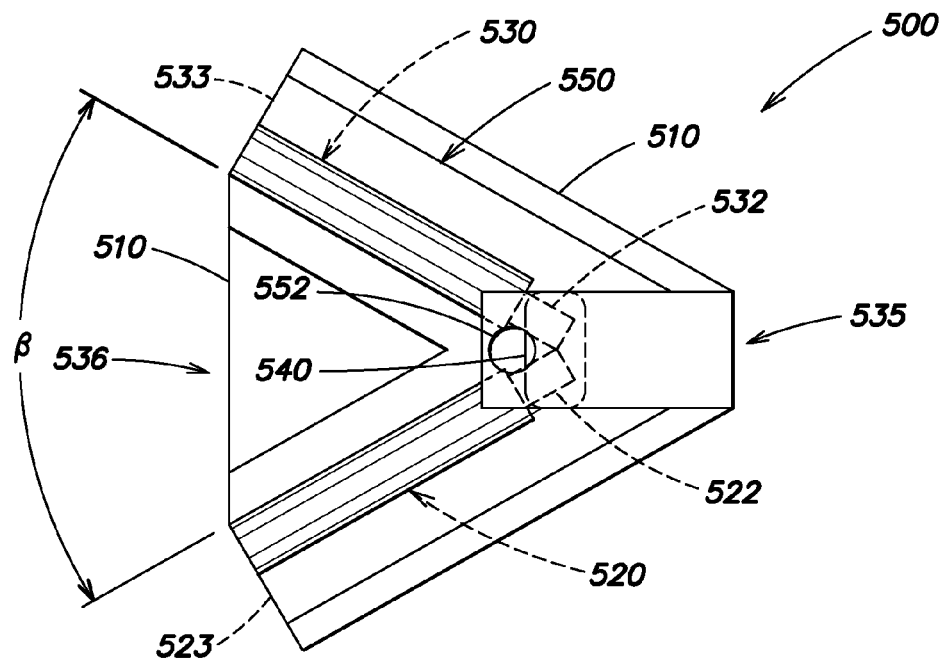
FIG. 5 is a top view of another exemplary embodiment of an analyte sensor according to the present invention.

The analyte sensor 100 may further include a second sensor member 130, which in some implementations may also include a semiconductor material. The second sensor member may include a core 132 comprised of a conductive material, and a cladding 134 comprised of a semiconductor material, for example. The materials for the second sensor member 130 may be the same as described above for the first sensor member 120. Optionally, the second sensor member 130 may be of more conventional materials, such as carbon, graphite, gold, silver, palladium or platinum. For example, the second sensor may be formed of a carbon/graphite PTF or Ag/AgCl. Preferably, however, the second sensor member 130 may be, as shown in FIG. 1, another fiber, which may be oriented in a generally parallel relationship to the first sensor member 120, and may comprise a semiconductor material. However, as is shown in FIG. 5, other orientations may be provided, such as non-parallel.

Again referring to FIGS. 1-3, applied onto the base 110 and in contact with, and electrically coupled to, at least the first sensor member 120 may be an active region 140 (which will be described more thoroughly below). Briefly, however, the active region 140 may be adapted to be exposed to the bio-fluid sample. The active region 140 may include one or more catalytic agents or reagents adapted to promote an electrochemical reaction between an analyte in the bio-fluid sample and the catalytic agents or reagents included in the active region 140. This produces reaction products and mobile electrons, which then may be conducted, for example, by the core 122 of the first sensor member 120. A mediator, to be described later herein, may be provided in the active region 140 to aid in carrying the electrons to the surface of the conducting core 122.

According to some embodiments of the invention, a cavity 155 may be formed and provided proximate to a working end 135 of the first sensor member 120 having the exposed core 122. The cavity 155 receives the bio-fluid sample inserted through an open end, for example. In particular, the cavity 155 may be at least partially formed and defined, for example, by inner surfaces of the lid 150, and surfaces of the base 110 (with active region 140 applied thereto). The cavity 155 may have any shape, but preferably has a shape, which promotes capillary action to cause a droplet of bio-fluid to drawn in and come to rest between the respective cores 122, 132 such that the sample is provided in contact with the active region 140. A hole 152 may be provided to assist capillary action of the bio-fluid. The cavity 155 may have a length of about 2-5 mm and a width of about 0.5 to 1.5 mm, for example.

In some embodiments, a sufficient bio-fluid sample for purposes of detecting an analyte concentration level may have a volume of less than about 0.5 microliters, less than about 0.3 microliters, or even less than about 0.2 microliters, for example. Other sample volumes may also be employed. Contributing to the need for a lessened volume of the bio-fluid sample may be the use of the fiber-like shape of the first sensor member 120. This may provide generally opposed surfaces 141W, 141R (wherein the W stands for "Working" and the R stands for "Reference") for the active region 140 to be applied to, a three dimensional shape, as well as a relatively large effective surface area of exposed electrode. As such, excellent analyte detection may be accomplished with a relatively small sample volume of the bio-fluid. Accordingly, the propensity to have to prick the finger, etc., a second time to obtain sufficient fluid volume for testing may be minimized or avoided.

Figure 4:
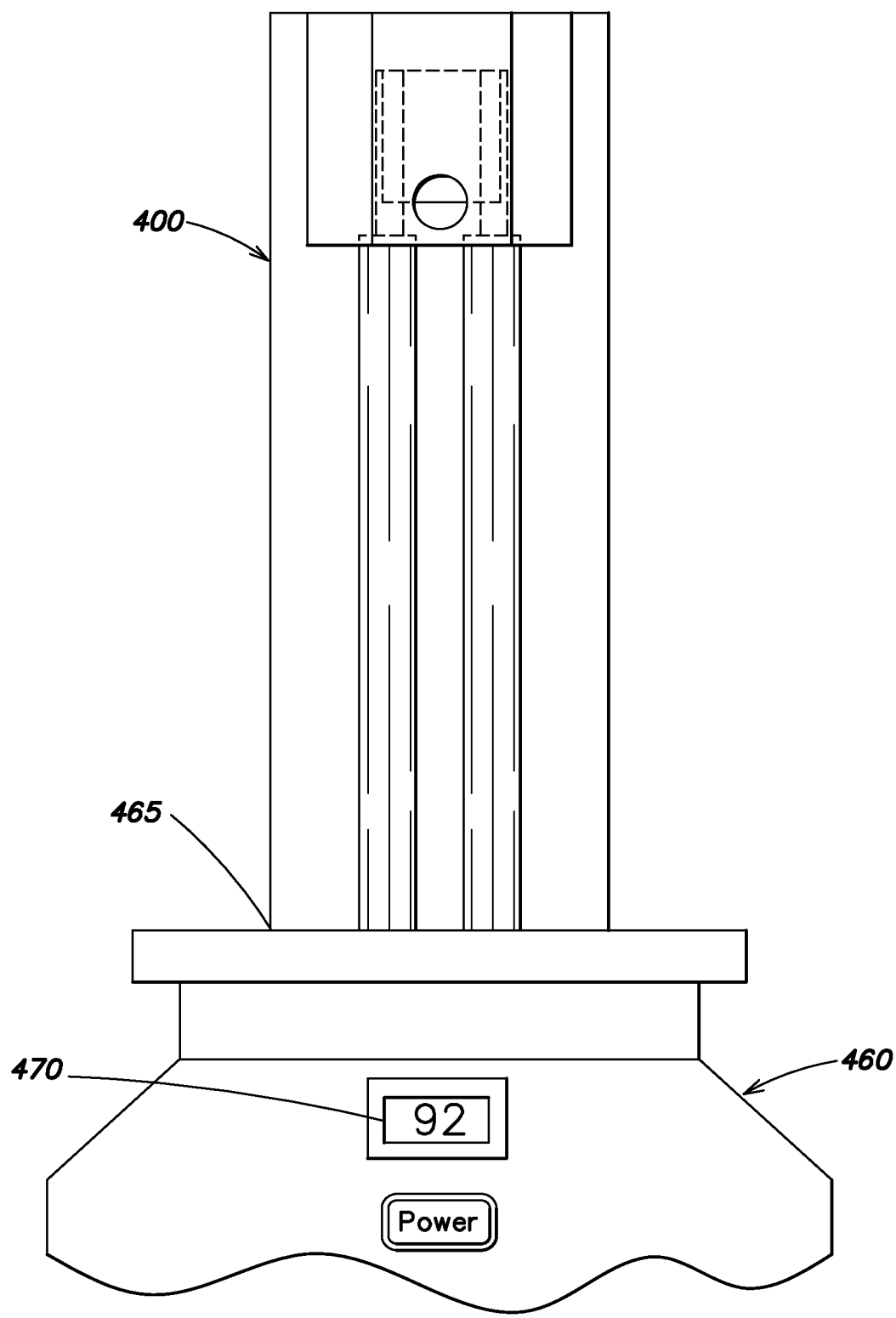
FIG. 4 is a frontal view of a testing apparatus including an exemplary embodiment of an analyte sensor received in a port of the apparatus according to the present invention.

Referring to FIG. 2, the active region 140 may be positioned within the cavity 155, and is preferably located at a bottom of the cavity 155, thereby allowing exposure of the active region 140 to the sample bio-fluid that enters the cavity 155. As shown, the active region 140 is applied over, and in contact with, the cores 122, 132. Upon insertion of the bio-fluid sample into the cavity 155, an electrochemical reaction takes place between the analyte in the fluid sample and the catalytic agents or reagents of the active region 140 to produce reaction products and generate the flow of electrons. The core 122 may then conduct and channel the electron flow and provide an electrical current, which may be proportional to the concentration of the analyte in the bio-fluid sample. This current may then be conditioned and displayed in any suitable readout form, such as in a digital readout 470 of a testing apparatus 460 (e.g., such as shown in FIG. 4).

As further shown in FIG. 4, an embodiment of an analyte sensor 400 such as the analyte sensor described with reference to FIGS. 1-3, or any of the additional embodiments described herein, may be inserted and received into a port 465 of the testing apparatus 460. Electrical contacts (not shown) in the apparatus 460 may come into electrical contact with conductive ends of sensor members 120, 130 (e.g., the cores and/or claddings thereof) thereby making an electrical connection to the circuitry of the apparatus 460. Upon applying a voltage bias (e.g., about 400 mV), conventional processing programs and circuitry may then equate the current supplied by the sensor member 120 to an analyte concentration level.

Again referring to FIGS. 1-3, one group of catalytic agents useful for providing the active region 140 may be the class of oxidase enzymes which includes, for example, glucose oxidase (which converts glucose), lactate oxidase (which converts lactate), and D-aspartate oxidase (which converts D-aspartate and D-glutamate). In embodiments in which glucose is the analyte of interest, glucose dehydrogenase (GDH) may optionally be used. Pyrolloquinoline quinine (PQQ) or flavin adenine dinucleotide (FAD) dependent may also be used. A more detailed list of oxidase enzymes which may be employed in the present invention is provided in U.S. Pat. No. 4,721,677, entitled "Implantable Gas-containing Biosensor and Method for Measuring an Analyte such as Glucose" to Clark Jr. which is hereby incorporated by reference herein in its entirety. Catalytic enzymes other than oxidase enzymes may also be used.

The active region 140 may include one or more layers (not explicitly shown) in which the catalytic agents (e.g., enzymes) and/or other reagents may be immobilized or deposited. The one or more layers may comprise various polymers, for example, including silicone-based or organic polymers such as polyvinylpyrrolidone, polyvinyl alcohol, polyethylene oxide, cellulosic polymers such as hydroxyethylcellulose or carboxymethyl cellulose, polyethylenes, polyurethanes, polypropylenes, polyterafluoroethylenes, block co-polymers, sol-gels, etc. A number of different techniques may be used to immobilize the enzymes in the one or more layers in the active region 140 including, but not limited to, coupling the enzymes to the lattice of a polymer matrix such as a sol gel, cross-linking the agents to a suitable matrix such as glutaraldehyde, electropolymerization, and formation of an array between the enzymes via covalent binding, or the like.

In some embodiments, an electrochemically active layer (not explicitly shown) may be positioned adjacent to an exposed end (e.g., the stripped portion) of the sensor member. The electrochemically active layer may include, for example, noble metals such as platinum, palladium, gold or rhodium, or other suitable materials. In a glucose detection embodiment, the active layer may undergo a redox reaction with hydrogen peroxide when polarized appropriately. The redox reaction causes an electrical current to be generated by electron transfer that is proportional to the concentration of the analyte that has been converted into hydrogen peroxide. This current may be conducted and conveyed from the electrochemically active layer through the core 122 and/or cladding 124 to a testing apparatus as previously described with reference to FIG. 4.

In some embodiments, a mediator may be within the active region 140 to promote the conversion of the analyte to detectable reaction products. Mediators comprise substances that act as intermediaries between the catalytic agent and the working electrode (e.g., the surface of the exposed core, a surface area enhancement of the core, or an electrochemically active layer applied to the core, etc.). For example, a mediator may promote electron transfer between the reaction center where catalytic breakdown of an analyte takes place and the working electrode, and may enhance electrochemical activity at the working electrode. Suitable mediators may include one or more of the following: metal complexes including ferrocene and its derivatives, ferrocyanide, phenothiazine derivatives, osmium complexes, quinines, phthalocyanines, organic dyes as well as other substances. In some embodiments, the mediators may be cross-linked along with catalytic agents directly to the working electrode.

As described above, the analyte sensor 100 may also include a second sensor member 130, which may function as a reference electrode providing a return path for an electrical current. In one or more embodiments, the second sensor member 130 may function as a counter electrode. As described further with reference to FIGS. 1-3 and 5-10B, the reference electrode may be arranged, formed and/or implemented in a number of different ways. In the embodiment depicted in FIGS. 1-3, the sensor member 130 may comprise a fiber mounted to the base 110 and may be comprised of a semiconductor material. For example, the sensor member 130 may include a conductive core 132 and may comprise a semiconducting cladding 134. However, it should be recognized that the reference electrode may take on other forms (e.g., a coil, foil, strip, or film) and may be made from other suitable materials, such as the materials described above.

To form an electrochemical cell, the second sensor member 130 may be coupled to the active region 140 in the cavity 155. In particular, the active region 140 may be applied to be in contact with and configured to extend between the cores 122, 132. The active region 140 may extend along the generally opposed surfaces 141W, 141R of the cores 122, 132 as best shown in FIG. 2, such that a drop of bio-fluid (depicted by dotted line 156) may be received in a three-dimensional feature formed by the active region 140 as applied over the surfaces of the cores 122, 132 and base 110.

FIG. 5 illustrates another embodiment of an analyte sensor 500 of the invention. As in the previously described embodiments, the first and second members 520, 530 may be mounted on a base 510 (e.g., of an insulating material) and an active region 540 may be applied to, preferably in contact with, the respective cores 522, 532 of the members. However, in this embodiment, the members may be oriented in other than a generally parallel relationship (e.g., at an angle β of greater than 0 degrees and less than or equal to 90 degrees). In other words, the spacing between the terminal ends 523, 533 of sensor members 520, 530 at the terminal end 536 may be greater than the spacing between the sensor members 520, 530 positioned in contact with the active region 540 at the working end 535. This configuration allows the sensor members 520, 530 and cores 522, 532 to be positioned very close together proximate the active region 540, but separates the terminal ends 523, 533 of the members 520, 532 for ease of electrical connection to a testing apparatus (not shown). A hole 552, for example, may allow venting for ease of insertion of the bio-fluid sample into an end of the cavity (not explicitly shown) which is formed by the cooperation of the lid 550 and the base 510 in the vicinity of the active region 540. Electrical connection with a testing apparatus may be made through electrical contact with the terminal ends 523, 533 of the sensor members 520, 530.

In order to enhance the effective conductive area of the conductive core 122 of the first member 120 in the embodiments shown in FIGS. 1-3 and FIG. 5, the cladding may be stripped off along a length of the fiber. Additionally or optionally, the inventors have discovered other mechanisms, which may be used for enhancing the effective conductive area of the working electrode in embodiments of the invention.

Figure 6:
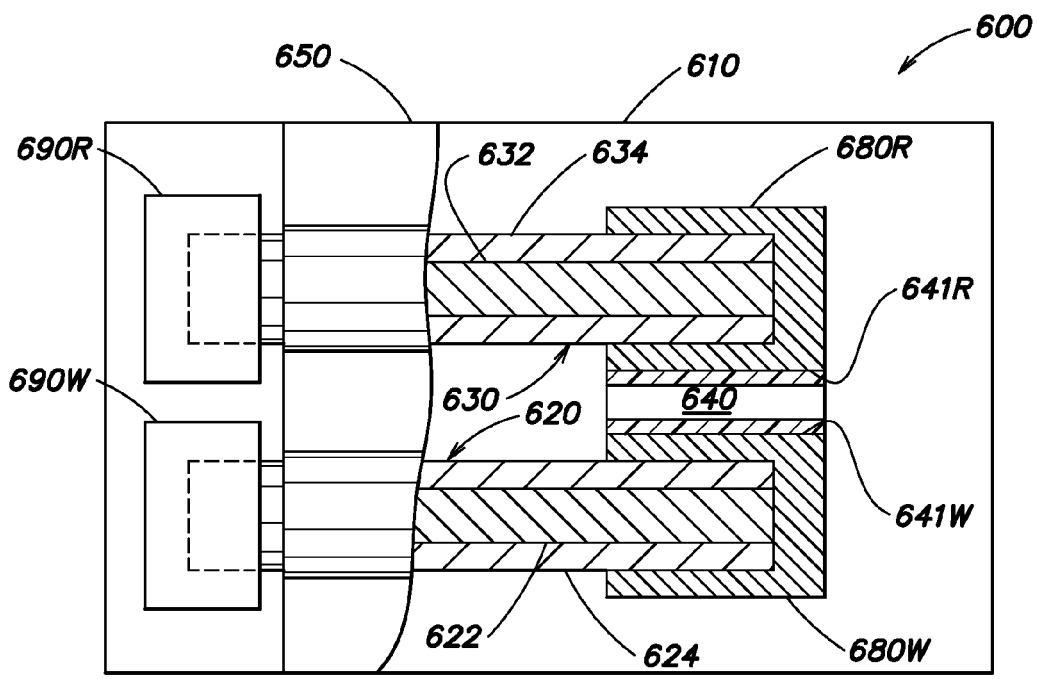
FIG. 6 is a partially cross-sectioned top view of another exemplary embodiment of an analyte sensor according to the present invention.

In FIG. 6, for example, a partially sectioned top view of another embodiment of an analyte sensor 600 is illustrated. In the embodiment depicted in FIG. 6, first and second sensor members 620, 630 may be mounted to a base 610 as in the previous embodiments. However, in this embodiment, an effective conductive area of the electrode may be increased by providing a conductive coating 680W on an end of the core 622. Similarly, the second sensor member 630 may include a coating 680R.

In this depicted embodiment, the active region 640 may be provided on the base 610 and in contact with the generally opposed surfaces 641W, 641R of the sensor members 620, 630. The coatings 680R, 680W may comprise carbon or any other suitable conductive material (e.g., Ag/AgCl, gold, silver, palladium, copper, aluminum, etc). In the present embodiment, the coatings 680W, 680R may be provided in electrical contact with simply cleaved ends of the cores 622, 632 and may be coated on the entire end of the members 620, 630, but may also be coated on peripheral surfaces of the claddings 624, 634. As such, the effective conductive area of the cores, which are exposed to the active region 640, may be substantially increased, in that the conductive coatings 680W, 680R function as extensions of the cores and the surfaces of the coatings 680W, 680R may become the working and reference electrodes, respectively. Accordingly, the active region 640 may be placed in contact with the cores 620, 630 over a relatively larger area. Optionally, the effective contact area of the cores may be enhanced by performing a cleave operation at the end of the members 120, 130 at other than a right angle (e.g., other than a simple cleave) thereby exposing more of the core.

Additionally shown in this embodiment of FIG. 6 is another method of providing an electrical contact between the analyte sensor 600 and a testing apparatus (not shown). In the previous embodiments, the electrical contact with the testing apparatus was by way of electrical contact with the terminal ends of the sensor members 120, 130 (FIGS. 1-3) and 520, 530 (FIG. 5). In contrast, the electrical contact in the current embodiment to the working and reference electrodes may be by contact with electrical contact patches 690W and 690R. The contact patches 690W, 690R are comprised of a conductive binding compound such as a conductive epoxy (e.g., silver epoxy or carbon epoxy) which is provided in contact with the cores 622, 632 and/or claddings 624, 634 of first and second sensor members 620, 630. As shown, a lid 650 may be coupled to the base 610 and may be dimensionally shorter than the base 610 so that the patches may be freely accessed by the test apparatus (not shown).

FIG. 7 is a top view of another embodiment of an analyte sensor 700 according to the present invention. The analyte sensor 700 comprises a first sensor member 720 and a second sensor member 730. Each of the sensor members 720, 730 may be comprised of a semiconductor material. For example, the members 720, 730 may include a core comprised of a conductive material and a cladding comprised of a semiconductor material. Each may be provided in the form of a fiber and may include the cladding surrounding the core along at least a portion of the length of the fiber. As in the previous embodiments, an active region 740 may be included in contact with at least the first sensor member 720, and may be provided in contact with both the first and second members 720, 730. In this embodiment, the fibers may include a curvature formed therein (shown exaggerated for clarity) such that the fibers at the working end 735 may be spaced closely together, yet the fibers at the terminal end 736 may be spaced further apart. This may allow adequate space for electrical connection to the contact patches 790W, 790R (of the type described with reference to FIG. 6).

Additionally in the depicted embodiment of FIG. 7, one or more of the sensor members 720, 730 of the analyte sensor 700 may be provided with a coded region 793. The coded region 793 may allow certain information to be coded onto one or more of the sensor members 720, 730. The coded information may relate to the properties and/or features of the sensor 700. For example, the date of manufacture, lot number, part number or version number, calibration data or constants, and/or expiration date may be encoded.

As best shown in enlarged view in FIG. 8, and in the case where a SiC cladding material is used, the coded region 793 may be formed of and include one or more changed conductivity tracks (e.g., rings) 795A-795C. The tracks may be formed on the cladding 724 of the first sensor member 720. The tracks 795A-795C may extend inwardly to the core 722. In the depicted embodiment, three changed conductivity tracks 795A-795C are shown. However a greater or lesser number of tracks may be used. For example, in one embodiment, a single track of variable width may be used, wherein a two point electrical measurement of resistance may be taken to measure and determine a level of resistance. That resistance value may then be correlated to a code in a lookup table, for example.

As shown in FIG. 9, a coded region 993 such as a changed conductivity track 995A may be formed, for example, by subjecting the SiC cladding 924 of the sensor member 920 to intense localized heat. For example, the cladding may be exposed to a laser beam 996 emitted from a laser 997 as the member 920 and the laser 997 are subjected to relative motion (designated by arrow 928). Once half the tracks are formed on one side, the fiber may be flipped over to form the other half of the track. For efficiency, many fibers may be aligned in a side-by-side configuration and may be treated at once. Other high intensity heat sources may be used, such as thermal plasma, for example. The intense localized heating of the cladding 924 comprised of SiC may cause a localized change in resistivity of the SiC cladding. As such, the localized heating may provide a changed conductivity track 995A encircling the core 922 which may preferably penetrate into the depth of the core 922. The track 995A may be of significantly different conductivity (e.g., several orders of magnitude or more) than the surrounding SiC material not subjected to heat treatment.

In the depicted embodiment of FIGS. 7-8, a plurality of spaced conductive tracks may be provided on the sensor member 720. The tracks positioned on the member 720 may be used to provide bits of coded information (e.g., 1's and 0's) which thereafter may be read from the member 720 by a suitable reader provided in the testing apparatus (not shown). For example, a track existing at a defined location spaced from the terminal end 736 of the sensor 700 may be used to signify a "1," while the absence of a track at a defined location (see location 791) may indicate a "0." Accordingly, with only 4 predetermined track locations, $2^4$ bits or 16 codes may be provided which then may be read by a testing apparatus (not shown), for example. For example, an electrical contact may contact each predetermined location to determine the presence or absence of the track. In some embodiments, in the alternative or in addition, it may be desirable to code information on the second member 730.

In the illustrated embodiment of FIG. 7, a subassembly is shown attached to the first sensor member 720. The subassembly comprises conductive patches 792, 794 and conductor 723. The purpose of the subassembly is to enable a reading of the presence or absence of a track or other coding. For example, there may be a circuit like the combination 792, 723, 794 for each track location such that the coding may be readily accessed at the end of the sensor 700.

Figure 10A:
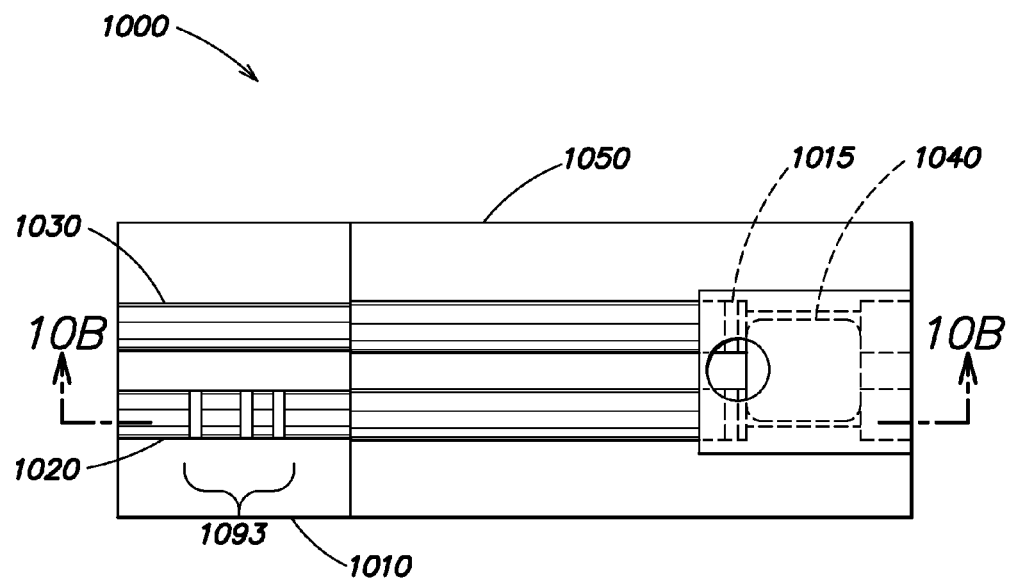
FIG. 10A is a top view of another exemplary embodiment of an analyte sensor according to the present invention.
Figure 10B:
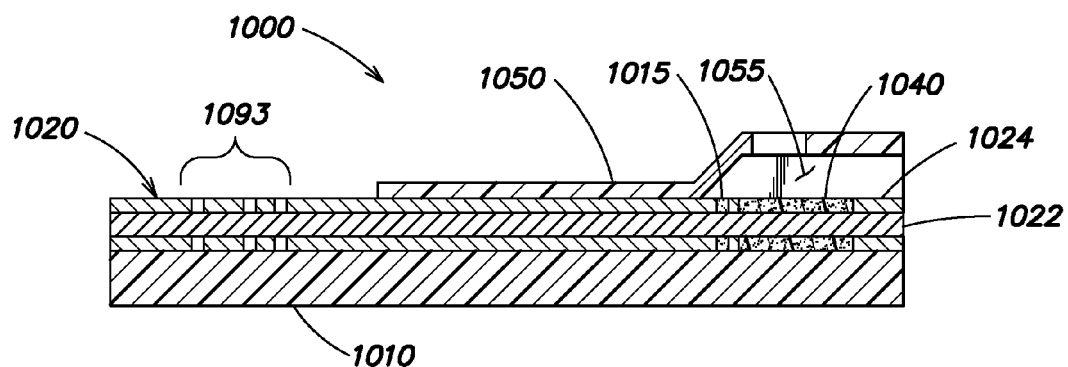
FIG. 10B is a cross-sectioned side view of the exemplary embodiment of FIG. 10A taken along section line 10B-10B.

Another embodiment of an analyte sensor 1000 according to the present invention is depicted in FIGS. 10A and 10B. The design of the sensor 1000 shown may be conducive to mass production manufacture of sensor strips. The analyte sensor 1000 may include a first sensor member 1020 and a second sensor member 1030. Each of the sensor members 1020, 1030 may be fibers, which may comprise a semiconductor material. For example, a core may be comprised of a conductive material and a cladding may be comprised of the semiconductor material. As in the previous embodiments, an active region 1040 may be included in contact with at least the first sensor member 1020, and preferably in contact with both the first and second members 1020, 1030. As configured, the first member 1020 may comprise a working electrode and the second member 1030 may comprise a reference or counter electrode. Furthermore, as in the previously depicted embodiment, one or more of the members 1020, 1030 may be provided with a coded region 1093 to allow information related to the properties and/or features of the sensor 1000 to be encoded. In this embodiment, the lid 1050 may be cut short to allow read access to the coded region.

In accordance with another aspect, a fill detector 1015 may be provided proximate to the active region 1040 to ensure that a sufficient bio-fluid sample is present when performing a detection of an analyte concentration. In the depicted embodiment, the fill detector 1015 may be provided by producing a conductive track on each of the members 1020, 1030 proximate the active region 1040 and preferably an equal distance therefrom. The tracks may be formed, as mentioned with reference to FIG. 9, by producing a localized zone of high conductivity on each sensor member 1020, 1030. The tracks may be located and included in the cavity 1055 formed between the base 1010 and lid 1050 as best shown in FIG. 10B. In operation, if a sufficient bio-fluid sample is present, a portion of the bio-fluid sample may come to rest between the tracks of the fill detector 1015 and may provide a conductive path through the fluid sample. Accordingly, when fluid is present at the location of the fill detector 1015, then a significant lowering of electrical resistance between the members 1020, 1030 may be measured.

In the illustrated embodiment, the active region 1040 may be applied in contact with an enhanced region formed on the member 1020. The enhanced region may include a high conductivity region which may be formed by removing a portion (e.g., stripping or etching) of the cladding 1024, as shown, such that the core 1022 is exposed in the proximity of the active region 1040. Optionally, an enhanced region may be locally produced by subjecting the fiber's cladding to intense localized heat and thereby causing a significant change in the resistivity and/or electrochemical activity of the cladding material. Thereafter, the active region 1040 may be applied to this enhanced region. Similar treatments may be applied to the second member 1030. Optionally, the active region may be applied to the cladding 1024 without being applied elsewhere, even on an end of the fiber.

Figure 11:
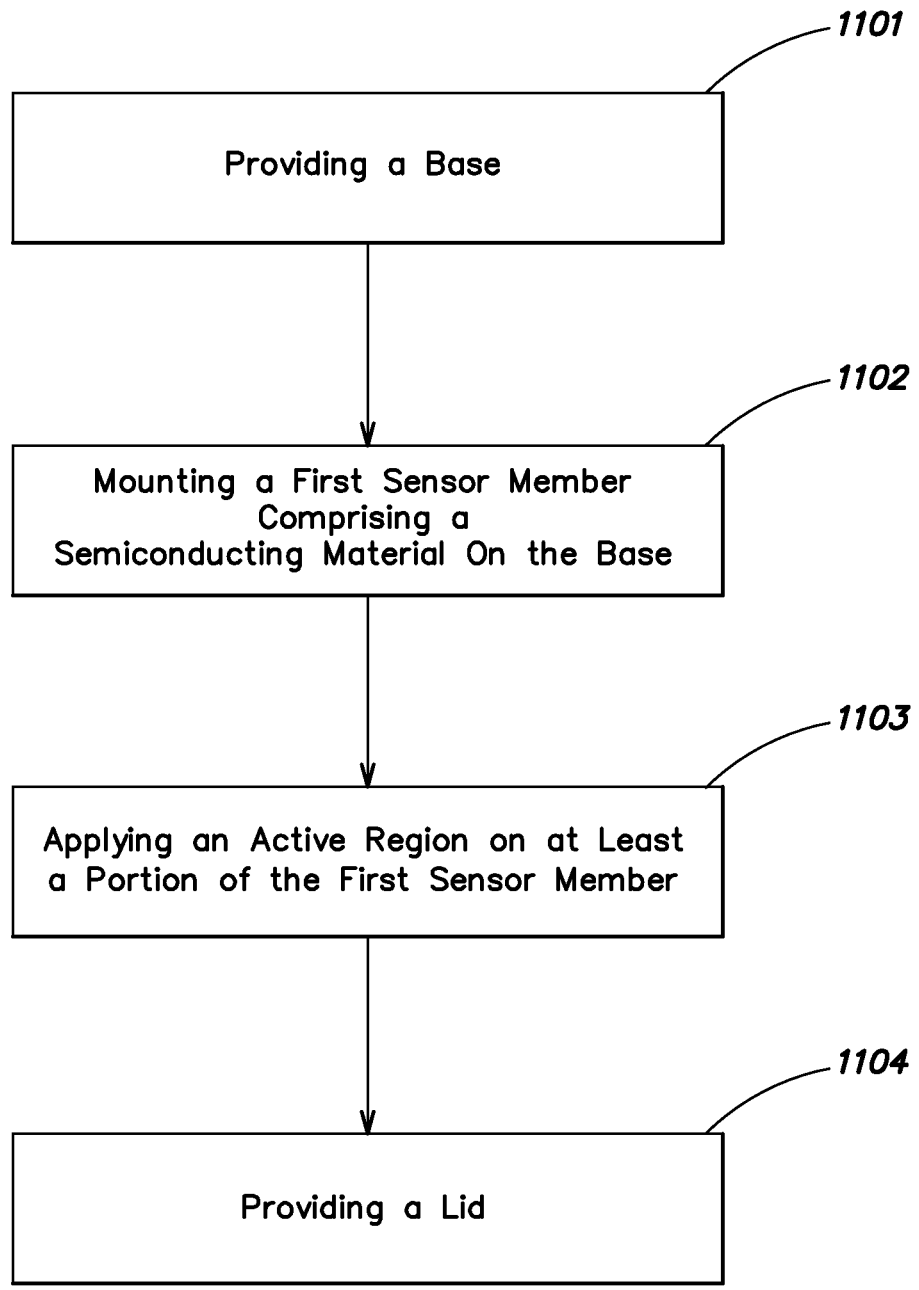
FIG. 11 is a flowchart illustrating methods of manufacturing the analyte sensor members according to the present invention.

Methods for manufacturing embodiments of the analyte sensors of the invention will now be described with reference to FIG. 11. Methods of manufacturing analyte sensors of the invention, may comprise the steps of providing a base (e.g., a base of insulating material) as in step 1101, mounting a first sensor member on the base wherein the first sensor member may be comprised of a semiconductor material (e.g., a conductive core and a semiconductor cladding) as in step 1102, applying an active region on a portion of the first sensor member as in step 1103, and providing a lid as in step 1104. The mounting of the sensor member may be by any of the mechanisms described above. Likewise, the step of applying the active region may be by any conventional process for applying such catalysts and/or reagents or as described above. Similarly, the lid may be provided and attached directly to the base, attached to the base via an adhesive layer, or attached to the base via securing the sensor member to the base and then securing the lid to the sensor member. The lid may extend along a full length of the base or only along a portion thereof. The lid may be preformed out of a deformable polymer material with suitable impressions formed therein for cooperating with the base and fibers to form the cavity. Likewise, the lid may include a hole (e.g., formed by cutting) for providing venting the cavity and to promote capillary action of the fluid sample.

Figure 12:
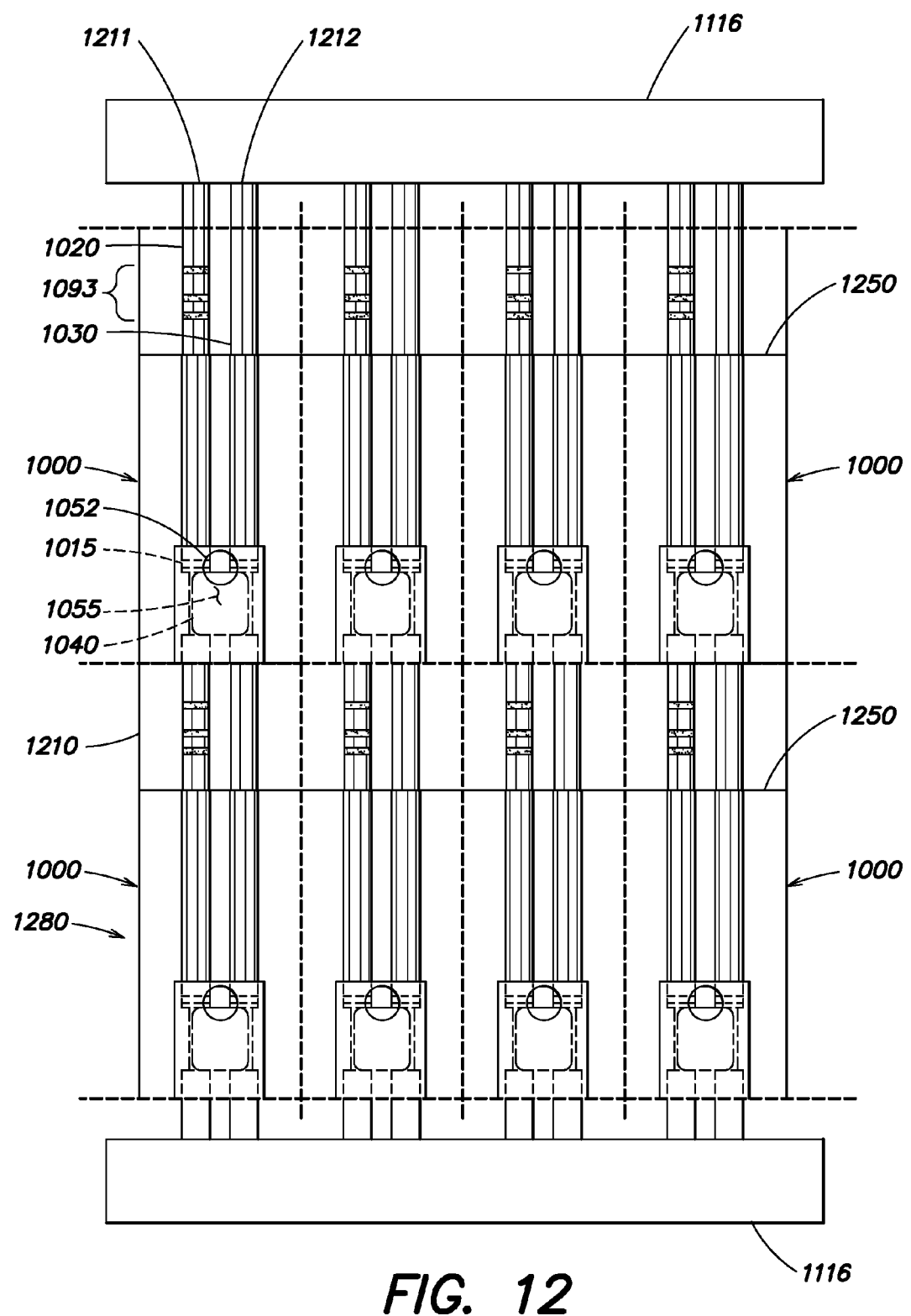
FIG. 12 is a top view illustrating a plurality of the analyte sensor members of FIG. 10A adapted to be cut from a larger unitary body.

Methods for manufacturing a plurality of the analyte sensors 1000 shown in FIGS. 10A-10B will now be described with reference to FIG. 12 and FIG. 13. Accordingly, a sheet of base material 1210, such as polycarbonate, may be provided. To the base material sheet 1210, a plurality of pairs of fibers 1211, 1212 having one or more segments of sensor members 1020, 1030 included therein may be mounted and held in place in registry with the base material 1210 by holders 1116, for example. Each of the fibers 1211, 1212 may comprise, in some embodiments, a semiconductor material (e.g., a conductive core and a semiconducting cladding such as SiC)) as heretofore described. Further, each of the fibers 1211, 1212 may include one or more high conductivity regions located along their length (e.g., a region of stripped cladding, a conductive coating region, etc.) or a region of enhanced activity (e.g., via laser treatment). The fibers 1211, 1212 may optionally include a fill detector 1015 as described with reference to FIGS. 10A and 10B and additionally or optionally may include one or more coded regions 1093, which may be used to code various features concerning the sensors 1000. The fibers 1211, 1212 may be preprocessed to include several regions of high conductivity, tracks for coded information and/or fill detectors in the manner described with reference to FIG. 9. The fibers 1211, 1212 may then be mounted on the base material 1110 by an adhesive, spot welding, ultrasonic welding, or by the application of heat and/or pressure. Optionally, they may be simply sandwiched between the base material sheet 1110 and the lid stock 1250 (to be described more fully below).

After the mounting of the fibers 1211, 1212, one or more active regions 1040 are applied atop the fibers (e.g., such as to the high conductivity regions) or otherwise along the length thereof where the analyte detection is to take place. The active regions 1040, as heretofore mentioned, may contain one or more catalytic agents or reagents (e.g., an enzyme) which may react with an analyte in the bio-fluid sample to produce a chemical species, which is electrochemically measurable. The active regions 1040 may be applied by layer-to-layer deposition, auto dispensing, dot drop, screen printing, or other like techniques. Following the formation of the active regions 1040, the lidstock 1250 may be applied over the fibers 1211, 1212 and base stock 1210. The lidstock 1250 may be attached to the base, the fibers, or both, such as by adhesive, heat, ultrasound or other welding techniques, or the like. Furthermore, the lidstock 1250 may contain numerous impressed regions having raised impressions formed therein, which when coupled with the base material and the fibers, form cavities 1055 adjacent to each active region 1040. Each cavity 1055 may include one or more holes 1052, preferably preformed in the lidstock 1250 prior to attachment, to allow for venting of the cavity, for example. The lidstock 1250 may be applied in strips if the direct access is needed to the coded regions 1093, or optionally, cutouts may be provided only in these regions of the lidstock 1250 to allow access.

Following assembly of the aforementioned components into a unitary body 1280, the individual sensor units (e.g., sensor 1000) may be cut using a die, laser, saw, or other suitable cutting technique. Thus, a plurality of analyte sensors 1000 may be manufactured from one unitary body 1280. Eight sensors 1000 are shown in FIG. 12. However, it should be recognized that methods of manufacturing more or less sensors may be adapted using the aforementioned method.

Figure 13:
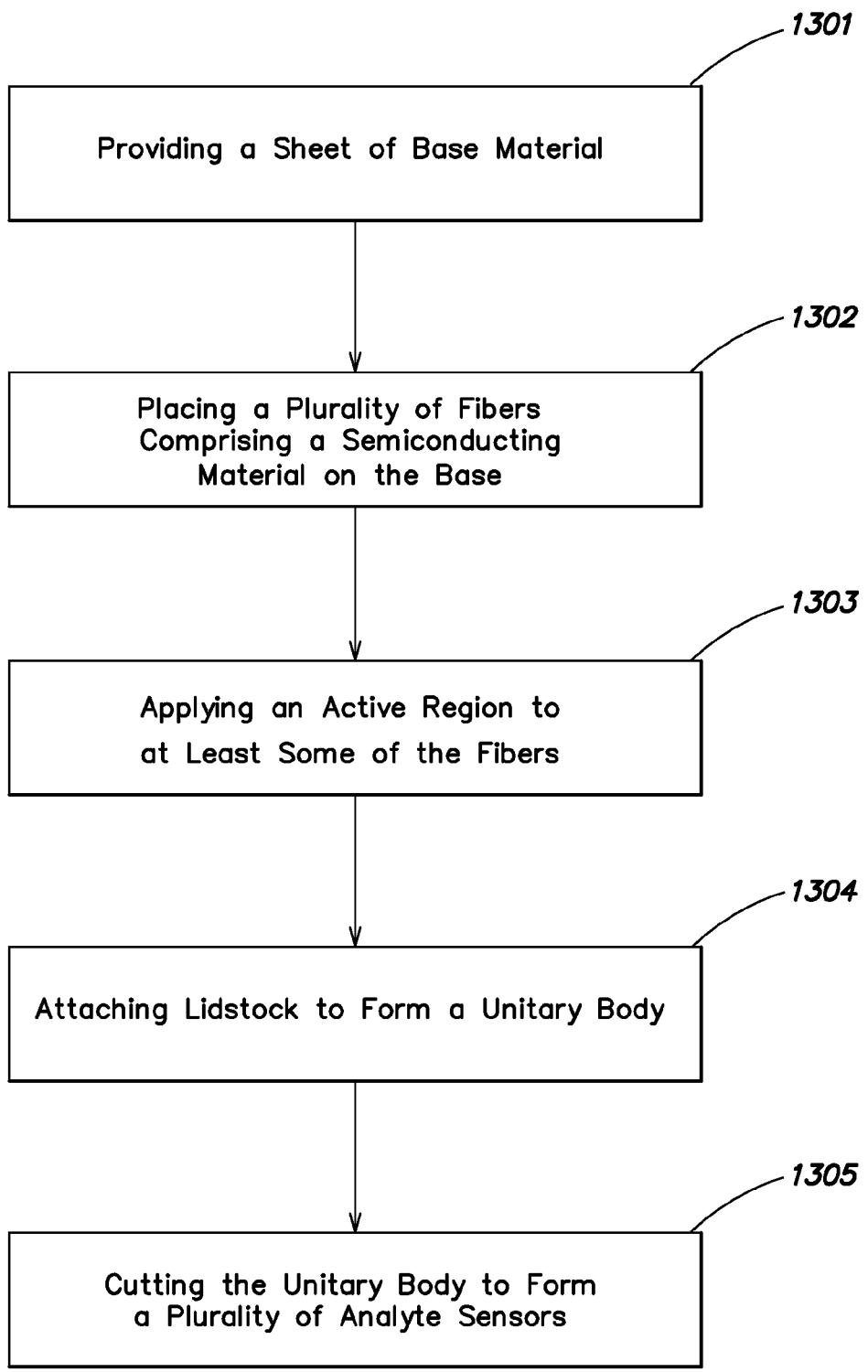
FIG. 13 is another flowchart illustrating methods of manufacturing a plurality of the analyte sensors according to the present invention.

In summary, and with reference to FIG. 13, a method of manufacturing analyte sensors of the invention, may comprise the steps of providing a sheet of base material (e.g., a base of insulating sheet material) as in step 1301, mounting a plurality of fibers on the sheet of base material wherein the fibers are comprised of a semiconductor material (e.g., conductive core and a semiconductor cladding) as shown in step 1302, applying an active region on a portion of at least some of the fibers as in step 1303, attaching lidstock as in step 1304 to form a unitary body, and cutting the formed unitary body to provide a plurality of analyte sensors as in step 1305.

The foregoing description discloses only exemplary embodiments of analyte sensors, apparatus including the same, and methods of manufacturing the sensors of the invention. Modifications of the above disclosed analyte sensors, apparatus incorporating them, and methods for manufacturing them, which fall within the scope of the invention, will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. An analyte sensor, comprising:
a base;
a first sensor member coupled to the base, the first sensor member comprising a semiconductor material;
a second sensor member coupled to the base and spaced from the first sensor member;
a lid coupled to the base and in contact with at least the first sensor member such that the first sensor member is sandwiched between the base and the lid; and
an active region in contact with at least the first sensor member,
wherein the first sensor member comprises a core of a conductive material and a cladding of the semiconductor material, and
wherein the semiconductor material comprises silicon carbide.

2. The analyte sensor of claim 1, wherein the second sensor member comprises a core of a conductive material, and a cladding of the semiconductor material.

3. The analyte sensor of claim 1, further comprising a lid coupled to the base and at least partially defining a cavity located proximate to the active region.

4. The analyte sensor of claim 1, wherein the first sensor member comprises a fiber.

5. The analyte sensor of claim 1, wherein a core of the first sensor member and a core of the second member are in contact with the active region.

6. The analyte sensor of claim 1, wherein the first sensor member comprises an enhanced region.

7. The analyte sensor of claim 6, wherein the enhanced region comprises an exposed portion of the core.

8. The analyte sensor of claim 6, wherein the enhanced region comprises a conductive coating.

9. The analyte sensor of claim 6, wherein the enhanced region comprises at least a portion of a cladding with an enhanced conductivity or electrochemical activity.

10. The analyte sensor of claim 1, further comprising a cavity at least partially formed between the base and the lid.

11. The analyte sensor of claim 10, wherein an end portion of the first sensor member and an end portion of a second member are located proximate to the cavity.

12. The analyte sensor of claim 1, wherein the cladding of first sensor member is partially impressed into the base.

13. The analyte sensor of claim 1, further comprising a fill detector.

14. The analyte sensor of claim 1, further comprising a coded region.

15. The analyte sensor of claim 1, wherein the analyte sensor is adapted to sense an analyte comprising one or more of glucose, lactate, aspartate, and glutamate.

16. The analyte sensor of claim 1, further comprising:
a cavity formed proximate to an end of the first sensor member; and
the active region positioned within the cavity, the active region being coupled to the end of the first sensor member.

17. The analyte sensor of claim 1, wherein the first sensor member comprises:
a fiber sensor member coupled to the base;
a cavity formed proximate to an end of the fiber sensor member; and
the active region positioned within the cavity, the active region being coupled to the end of the fiber sensor member.

18. The analyte sensor of claim 1, wherein:
the base is an insulating material;
the second sensor member comprises a core of conductive material and a cladding of a semiconductor material surrounding the core;
a cavity is formed proximate to ends of the first and second sensor members;
the active region is positioned within the cavity, the active region being coupled to both the first and second sensor members; and
the base and lid at least partially define the cavity.

* * * * *